United States Patent

Subramanyam et al.

[11] Patent Number: 5,523,324
[45] Date of Patent: Jun. 4, 1996

[54] COMPOSITION

[75] Inventors: Ravi Subramanyam, North Brunswick; Ben Gu, East Brunswick, both of N.J.

[73] Assignee: Colgate-Palmolive Company, New York, N.Y.

[21] Appl. No.: 279,137

[22] Filed: Jul. 22, 1994

Related U.S. Application Data

[63] Continuation of Ser. No. 84,854, Jun. 30, 1993, abandoned.
[51] Int. Cl.$^6$ .................. A61K 31/17; A61K 31/045
[52] U.S. Cl. .................. 514/596; 514/724; 514/738
[58] Field of Search .................. 514/596, 724, 514/738

[56] References Cited

U.S. PATENT DOCUMENTS

| | | |
|---|---|---|
| 3,723,326 | 3/1973 | Cheng . |
| 4,832,861 | 5/1989 | Resch . |
| 4,954,281 | 9/1990 | Resch . |
| 5,006,529 | 4/1991 | Resch . |
| 5,310,508 | 5/1994 | Subramanyam et al. .............. 252/549 |

FOREIGN PATENT DOCUMENTS 1197817  7/1970  United Kingdom .

OTHER PUBLICATIONS

Handbook of Surfactantss, M. R. Porter, 1991, pp. 85–86.

*Primary Examiner*—Zohreh Fay
*Attorney, Agent, or Firm*—Martin Barancik

[57] ABSTRACT

An aqueous composition comprising
a. a suffactant selected from the group consisting
(1) a salt of the formula

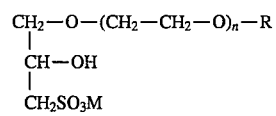

wherein R is an aliphatic radical or mixed aliphatic radicals with 4 to 24 carbon atoms, inclusive, the average value of n is from one to about 10, and M is a metal or amine,
(2) a salt of an acyl isethionate wherein the acyl group is from about 10 to 22 carbon atoms inclusive,
(3) mixtures of (1) and (2), and
b. an antibacterial effective amount of

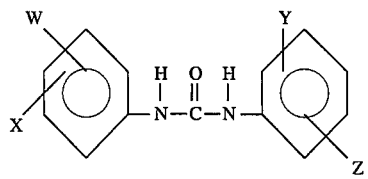

wherein W, X, Y and Z are halogen hydrogen or trifluoroethyl with the proviso that at least three of W, X, Y and Z are halogen or trifluoromethyl,
wherein a. is present in the composition in sufficient amounts to increase the antibacterial efficacy of b.

12 Claims, No Drawings

COMPOSITION

This is a Continuation, of application Ser. No. 08/084,854 filed Jun. 30, 1993 now abandoned.

BACKGROUND OF THE INVENTION

Skin cleansing agents have been used for many years for removing soil from the human body. In the constant process of improving appearance, health and odor, additives have been added to cleansing formulations. Examples of additives include emollients for better skin conditioning and feel, synthetic surfactants for better lathering and/or mildness, and antibacterial agents. These antibacterial agents cause reduction of bacteria living on the skin thereby bringing about a potentially healthier surface as well as reduced odor arising from the bacteria. A number of antibacterial agents have been developed and employed in cleansing formulations over the years, including hexachlorophene, halogenated carbanilides and halogenated and hydroxy substituted diphenylethers. These substances have been used with a variety of surfactants in various formulations. Such surfactants include soaps e.g. fatty acid carboxylate salts such as sodium stearate, potassium palmitate and the like, long chain alkyl sulfates such as sodium lauryl sulfate and potassium palimityl sulfate; long chain alkyl sulfonates such as sodium lauryl sulfonate and derivatives thereof such as sodium cocoylisethionate; alkylsulfosuccinates such as sodium octyl sulfosuccinate, and the like. Additional well known surfactants such as alkyl glyceryl sulfonate, also known as AGES, have also been employed.

Certain combinations of various surfactants and antibacterial agents are disclosed as providing greater antibacterial activity than the antibacterial agent alone. For example, U.S. Pat. No. 4,111,844 discloses that certain chlorinated ortho-hydroxyldiphenylethers in combination with specific surfactants such as alkylsulfonates, alkylsulfates, alkylnaphthalene sulphonates and dialkylsulfosuccinates when used in certain ratios provide better antibacterial activity than the antibacterial agent alone. Triclosan is the preferred antibacterial agent. Other combinations of surfactants and antibacterial agents are shown in the following patents.

U.S. Pat. No. 5,006,529—discloses combinations of soap, cocoylisethionate salt, isethionate salt, free fatty acid and triclosan in certain ratios.

U.S. Pat. No. 4,954.281—discloses combinations of soap, alkyl glycerol ether sulfonate and triclosan in certain ratios, with or without free fatty acid.

U.S. Pat. No. 4,832,861—discloses combinations of soap, cocoylisethionate salt, isethionate salt, free fatty acid and triclosan in certain ratios.

U.S. Pat. No. 3,723,326—discloses combinations of soap wherein greater than 50% of the metal ion is potassium, free fatty acid, opacifying agent, alkyl cellulose, and a mixture of triclosan, a trichloro carbanilide and a dichloro trifluoromethyl carbanilide in certain ratios.

GB 1,197,817 discloses combinations of soap and mixtures of triclosan, trichlorocarbanilide, and dichlorotrifluoromethylcarbanilide.

A new combination of specific surfactants and antibacterial agents has been discovered which brings about greater antibacterial activity than the antibacterial agent without the-suffactant(s).

SUMMARY OF THE INVENTION

In accordance with the invention there is an aqueous composition comprising a. a surfactant selected from the group consisting of
(1) a salt of the formula

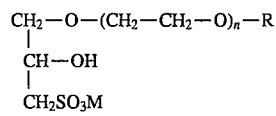

wherein R is an aliphatic radical or mixed aliphatic radicals with 4 to 24 carbon atoms, inclusive, the average value of n is from one to about 10, and M is a metal or amine, (2) a salt of an acyl isethionate wherein the acyl group is from about 10 to 22 carbon atoms inclusive, or (3) mixtures of (1) and (2), and b. an antibacterial effective amount of

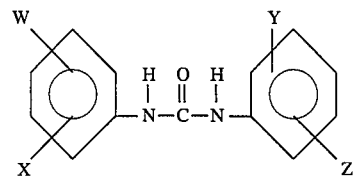

wherein W, X, Y and Z are halogen, hydrogen or trifluormethyl with the proviso that at least three of W, X, Y and Z are halogen or trifluoromethyl, wherein a. is present in the composition in sufficient amounts to increase the antibacterial efficacy of b.

DETAILED DESCRIPTION OF THE INVENTION

The surfactant a (1) is an ethoxylated aliphatic glyceryl sulfonate salt. The average number of ethoxyl groups is preferably from one to four as values for n. The R group is an aliphatic such as alkyl, alkenyl, cycloaliphatic, alkyl substituted cycloaliphatic and the like. The alkyl and alkenyl groups are normal or branched, preferably normal. The preferred groups are alkyl and alkenyl. Alkyl is most preferred. The number of carbon atoms in R is 4 to 24 carbon atoms, inclusive, preferred is 8–22 and most preferred is 10–20 carbon atoms, inclusive. Samples of such groups include decyl, lauryl, myristyl, palmityl, stearyl and eicosyl.

With respect to a (2) compounds the acyl groupings is from about 10 to 22 carbon atoms, inclusive, preferably 12 to 20 carbon atoms. The acyl group is alkyl or alkenyl, preferably alkyl and branched or normal, more preferably normal. Mixtures of these materials can be used, particularly as natural acids, to acylate the isethonic acid or isethionate.

The salts of the composition components are present as the metal or amine cation. Examples of such metals are the alkali metals such as sodium, potassium and lithium. Other metals can be employed as long as the water solubility of the salt is maintained. Sodium salts are preferred. Amines or substituted amines can be employed in the salt form. Example of such amines include triethylamine, ammonia, tribulylamine, triethanolamine, tris (hydroxymethyl) aminomethane, and the like.

The wt % of component "a" of the composition is sufficient to bring about increased antibacterial activity of component "b". Generally a miniumum of about 1 wt % of a is required. It is preferred to use a minimum of about 4 wt %., more preferably 6 wt %. The effect is seen at relatively high wt ratios of a to b. However, generally no more than about 35 wt % of a is used preferably no more than about 25 wt %, most preferably no more than about 20 wt %.

Component b of the claimed composition is an antibacterial agent of the formula.

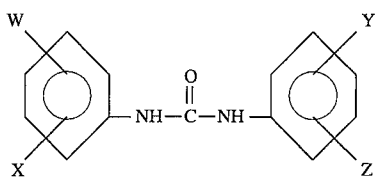

wherein W, X, Y and Z are the same or different and are halogen, trifluoromethyl or hydrogen. Halogen is fluoro, chloro, bromo, or iodo. The preferable halogen are chloro or bromo, most preferably chloro. Generally three of W, X, Y and Z are halogen and/or trifluromethyl, preferably all halogen. The most preferable compound of the formula is generically known as triclorcarban or trichlorocarbanilide; CAS number 101-20-2. With respect to the schematic formula above, triclocarban occurs when W is meta chloro, X is para chloro, Y is para' chloro and Z is hydrogen. Wt % of the antibacterial agents are not unduly significant; however, there should generally be enough to provide effective, relatively long lasting antibacterial effect on the skin or hair when such agent is evenly dispersed throughout the cleansing composition. Generally, a minimum of about 0.1 wt % of the agent is usually employed. More agent can be used, the upper limit depending upon such factors as compatibility, irritancy, cost and the like. Generally no more than about 1.0 wt % of the compositon is employed. A further range is about 0.2 to 0.8 wt %.

Other components may be present in the aqueous composition. Soap is the most common material present in the composition. When utilizing a soap it is preferably a tallowate, cocoate or palm kernalate type, usually in the sodium salt form. When more than one soap is present, the ratio of tallow fatty acid to coconut oil fatty acid can range from about 40 wt % to about 90 wt % sapionified tallow fatty acid and from about ten to about 60 wt % sapionified coconut oil fatty acid. Such soaps can be "superfatted" as well through the addition of quantities of free fatty acid such as stearic acid, palmitic acid or other long chain fatty acids. Wt % of the acids are from about 1.0 to about 10.0 of the composition. Generally if the soap is present in the composition, it is from about 5 wt % to about 95 wt % of the composition, preferably 10 to 90 wt % of the composition.

Additional synthetic surfactants can also be present. Examples of these surfactants are described at U.S. Pat. No. 5,139,781 issued to Cheseborough Ponds, column 5, line 25 to column 9, line 52, herein incorporated by references.

Classes of other materials which can be present are emollients, thickeners, structurants, fragrances, and the like. Moisture or water can also be present and often time comprises the remainder of the aqueous composition.

The composition can take the form of a liquid such as a liquid soap, shampoo, bubble bath, shower gel and the like or a solid form such as a bar which can illustratively be a soap, combar or syndet composition.

Below are examples of the invention. These examples are illustrative of the generic nature of the invention and are not intended to limit such invention.

The test used to measure the antibacterial activity of the composition is a typical zone of inhibition test (Disc Diffusion Method) utilizing *Staphylococcus aureus* (ATCC 6538) conducted according to the following procedure.

1. Preparation of Test Organism

Organisms (S. aureus) are grown in 10 ml of Tryptic Soy Broth (substituted for Antibiotic Medium 3) for 24 hours at 37 C.

11. Preparation of Plates

The base layer is prepared with Tryptic Soy Agar (substituted for Antibiotic Medium 2). 20 ml of prepared agar is dispensed into 25 mm test tubes and sterilized. Pour the agar into heavy bottom Petri dishes and allow to solidify undisturbed.

Trypic Soy Agar is used to prepare the seed layer. 100 ml of prepared agar is dispensed into a screw capped flask. After sterilization the flask is cooled to 45° C. in a water bath.

2 ml of bacterial culture (in Part 1) is inoculated into Seed Agar. The seed agar is gently mixed and maintained at a temperature of 45° C. Pipet 7 ml of the seed agar onto the Base Agar plate and evenly cover the surface.

111. Preparation of Sample

Penicillin assay discs are inoculated with 20 microliter of sample (4% soap solution) by using a micropipet i.e. discs are air-dried in a disposable petri dish at RT for one hour.

IV. Placement of Disc and Reading of Zone

The discs with different samples are placed on seeded plate. Control discs are treated with 4% 60/40 (soap)/3.5/3.5 (free fatty acid) soap solution. Replicates of 3 plates are tested. The plates are incubated for 24 hours at 37° C. The diameter of the zones of inhibition is measured using Omega Slide Caliper in mm; NI indicates no inhibition.

The higher reading of zone inhibition indicates the greater antibacterial activity. In the tables below the following abbreviations are used:

Soap—a long chain alkylcarboxylate salt mixture comprised of 60 wt % tallow based soaps and 40 wt % coco based soaps. Also present is 7 wt % free fatty acids. The remainder of the composition is water.

TCC is Triclocarbon; 3, 4, 4'-trichlorocarbanilide.

SCI is sodium cocoylisethionate.

NEGS is ethoxylated sodium alkyl glyceryl ether sulfonate.

wherein the average number of ethyoxyl groups is 1 and the alkyl has from 14 to 15 carbon atoms.

DP-300 is triclosan, 4, 2', 4'-trichloro -2-hydroxydiphenylether.

When a certain amount of NEGS or SCI is present in a composition, the quantity of soaps present has been reduced by that wt % of NEGS or SCI. All system numbers are in weight %.

Below are the results:

EXAMPLE 1

| System | Zone diameter and standard deviation, mm. |
|---|---|
| Soap | NI |
| Soap + 0.3 TCC | 8.7 ± 0.1 |
| Soap + 0.5 TCC | 8.8 ± 0.1 |
| Soap + 0.7 TCC | 8.7 ± 0.1 |
| Soap + 15% SCI + 0.3 TCC | 9.2 ± 0.1 |
| Soap + 15% NEGS + 0.3 TCC | 9.8 ± 0.2 |
| Soap + 8% SCI + 7% NEGS + 0.3 TCC | 9.6 ± 0.1 |

As is clearly shown from the data, the use of NEGS combined with TCC brings about a substantially increased inhibition of staph aureus growth. This inhibition is greater than either SCI alone or SCI and NEGS together. All of these inhibitions are significantly greater than TCC alone with soap.

COMPARATIVE EXAMPLE 1

The same test system was employed to assess the value of NEGS and/or SCI as a bacterial inhibition enhancer when used in combination with DP-300. Below are the results:

| System | Zone diameter and standard deviation, mm. |
|---|---|
| Soap | NI |
| Soap + 0.3% DP-300 | 22.7 ± 0.4 |
| Soap + 22% SCI + 0.3 DP-300 | 23.5 ± 0.2 |
| Soap + 22% NEGS + 0.3 DP-300 | 23.6 ± 0.1 |
| Soap + 11 % NEGS + 11% SCI + 0.3 DP-300 | 23.5 ± 0.1 |
| Lever 2000 | 23.1 ± 0.1 |

This data shows that neither SCI nor NEGS brings about significantly increased antibacterial effectiveness when used in combination with DP-300, another well known antibacterial agent. These results emphasizes the surprising nature and selectively of the claimed invention.

We claim:

1. An aqueous solid, liquid or gel composition comprising
   a. a surfactant selected from the group consisting of
      (1) a salt of the formula

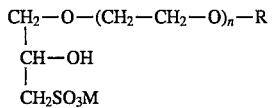

wherein R is an aliphatic radical or mixed aliphatic radicals with 4 to 24 carbon atoms, inclusive, the average value of n is from one to about 10, and M is a metal or amine,
      (2) a salt of an acyl isethionate wherein the acyl group is from about 10 to 22 carbon atoms inclusive,
      (3) mixtures of (1) and (2), and
   b. an antibacterial effective amount of

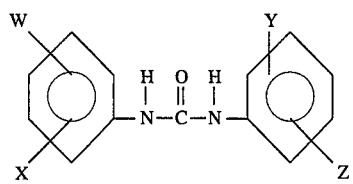

wherein W, X, Y and Z are halogen hydrogen or trifluormethyl with the proviso that at least three of W, X, Y and Z are halogen or trifluoromethyl, wherein a. is present in the composition in sufficient amounts to increase the antibacterial efficacy of b with the proviso that a is a(1) or a(3).

2. The composition in accordance with claim 1 Wherein R is 8 to 22 carbon atoms, inclusive; n is average value of 1 to 4; W, X and Y are the same or different and are halogen or trifluormethyl, Z is hydrogen, and acyl is 10 to 20 carbon atoms.

3. The composition in accordance with claim 2 wherein W, X, and Y are halogen.

4. The composition in accordance with claim 3 wherein W, X and Y are chloro.

5. The composition in accordance with claim 4 wherein W is 3-chloro, X is 4-chloro, Y is 4'-chloro; trichlorocarbanilide.

6. The composition in accordance with claim 2 wherein a is from about 1 to 35 wt % of the composition and b is from about 0.1 to 1.0 wt % of the composition.

7. The composition in accordance with claim 6 wherein about 0.2 to 0.8 wt % of b is present and about 4 to 25 wt % a is present.

8. The composition in accordance with claim 6 wherein 5 to 95 wt % of a soap is present.

9. The composition in accordance with claim 3 wherein a is from about 1 to 35 wt % and b is from about 0.1 to 1.0 wt %.

10. The composition in accordance with claim 5 wherein a is from about 1 to 35 wt %, b is from about 0.1 to 1.0 wt % and in addition about 5 to 95 wt % of the composition is a soap.

11. The composition in accordance with any of claims 1–10 wherein surfactant a is a (1).

12. The composition in accordance with any of claims 1–10 wherein surfactant a is a (3).

* * * * *